(12) United States Patent
Vanzieleghem et al.

(10) Patent No.: US 11,596,705 B2
(45) Date of Patent: Mar. 7, 2023

(54) KIT FOR DETECTING RESIDUAL CONTAMINATIONS ON MEDICAL DEVICES

(71) Applicant: ONELIFE S.A., Louvain-la-Neuve (BE)

(72) Inventors: Thomas Vanzieleghem, Louvain-la-Neuve (BE); Sébastien Fastrez, Mons (BE)

(73) Assignee: ONELIFE S.A., Louvain-la-Neuve (BE)

( * ) Notice: Subject to any disclaimer, the term of this patent is extended or adjusted under 35 U.S.C. 154(b) by 325 days.

(21) Appl. No.: 16/759,166

(22) PCT Filed: Oct. 26, 2018

(86) PCT No.: PCT/EP2018/079475
§ 371 (c)(1),
(2) Date: Apr. 24, 2020

(87) PCT Pub. No.: WO2019/081744
PCT Pub. Date: May 2, 2019

(65) Prior Publication Data
US 2020/0276347 A1 Sep. 3, 2020

(30) Foreign Application Priority Data
Oct. 27, 2017 (BE) .................................. 2017/5778
Apr. 30, 2018 (BE) .................................. 2018/0058

(51) Int. Cl.
*A61L 2/28* (2006.01)
*C11D 3/386* (2006.01)
*C11D 3/40* (2006.01)
*C11D 3/48* (2006.01)
*G01N 31/22* (2006.01)

(52) U.S. Cl.
CPC ................ *A61L 2/28* (2013.01); *C11D 3/386* (2013.01); *C11D 3/40* (2013.01); *C11D 3/48* (2013.01); *G01N 31/226* (2013.01); *A61L 2202/24* (2013.01)

(58) Field of Classification Search
CPC ........ A61L 2/28; A61L 2202/24; C11D 3/386; C11D 3/40; C11D 3/48; G01N 31/226; G01N 31/22; G01N 31/00; C09B 67/00
See application file for complete search history.

(56) References Cited

U.S. PATENT DOCUMENTS

| 9,474,282 B2 * | 10/2016 | Hall ...................... A61K 47/12 |
| 10,683,529 B2 * | 6/2020 | Boels ....................... C12Q 1/22 |
| 2014/0113326 A1 | 4/2014 | Boels et al. |

FOREIGN PATENT DOCUMENTS

| DE | 102006062379 A1 | 6/2008 |
| EP | 2537601 A1 | 12/2012 |
| EP | 2789682 A1 | 10/2014 |
| JP | 61-164158 A | 7/1986 |
| WO | 2014/079938 A1 | 5/2014 |

OTHER PUBLICATIONS

International Search Report from International Application No. PCT/EP2018/079475, dated Jan. 14, 2019.
Written Opinion from International Application No. PCT/EP2018/079475, dated Jan. 14, 2019.
English Translation of the Written Opinion from International Application No. PCT/EP2018/079475, dated Jan. 14, 2019.
Smith et al., "Quantitative analysis of residual protein contamination of podiatry instruments reprocessed through local and central decontamination units", Journal of Foot and Ankle Research, 4:2, 7 pages (2011).
Database WPI 15, Week 198636, Thomson Scientific, London, GB; AN 1986-235291, XP002787408 (1986).
"Rapid ethanol-based coomassie blue staining", Oct. 14, 2017 (Oct. 14, 2017), XP002787409. Retrieved from the Internet: URL: https://web.archive.org/web/20170912073147/http://www.mundilab.com/protocolos/PAGE-destain.html [retrieved on Dec. 12, 2018].

* cited by examiner

*Primary Examiner* — David P Porta
*Assistant Examiner* — Fani Polyzos Boosalis
(74) *Attorney, Agent, or Firm* — Merchant & Gould P.C.

(57) ABSTRACT

The present invention relates to a kit for checking the quality of cleaning of medical devices in situ comprising a staining solution by soaking comprising a colorant in a dilution phase compatible with the requirements of the medical environment, and a developing solution by soaking comprising said dilution phase.

16 Claims, No Drawings

KIT FOR DETECTING RESIDUAL CONTAMINATIONS ON MEDICAL DEVICES

This application is a National Stage Application of International Application No. PCT/EP2018/079475, filed 26 Oct. 2018, which claims benefit of Serial No. 2018/0058, filed 30 Apr. 2018 in Belgium and Serial No. 2017/5778, filed 27 Oct. 2017 in Belgium and which applications are incorporated herein by reference. To the extent appropriate, a claim of priority is made to each of the above-disclosed applications.

The present invention relates to a kit for checking the quality of cleaning of medical devices.

Re-treating medical devices consists of applying cleaning conditions according to standards which have been clearly defined in Europe and on a global level. This enables the elimination of bacteria, biofilms and organic soils which contaminate medical devices after use. Indeed, they have been in contact with patients, for example, during a surgical operation or during an appointment at the dentist. To be able to reuse these medical devices entirely safely, it is essential to be able to clean and then sterilise them effectively in order to be able to reuse them for other medical interventions.

These medical devices typically have parts referred to as invasive and non-invasive, as defined with respect to the parts of the medical devices which come into contact either with organic materials and/or protein compounds and/or biofilms, or with the gloves or hands of a practitioner respectively.

It is true that the invasive parts found on medical devices are the most likely to come directly into contact with the blood or organs of the patient. Therefore, it is the invasive parts of medical devices which require particular attention as it is necessary that no trace of organic or biological contamination remain on the medical devices after sterilisation. It is understood that the non-invasive parts of the medical devices must also be considered as it cannot be ruled out that they are also contaminated if they come into contact with the invasive parts of other medical devices.

Thus, the sterilisation process can only be guaranteed if the medical devices no longer show detectable organic contamination. It is therefore desirable to sterilise the equipment in order for it to be sufficiently clean, so it no longer shows detectable protein compounds and/or organic materials and/or biofilms.

Contamination which generally develops in hospital environments is a public health problem which health professionals wish to reduce or even, if possible, eradicate. The consequences linked to diseases such as Creutzfeldt-Jakob disease or nosocomial infections are known without having to be cited here. In patent application WO 2014079938 A1, quality cleaning of medical instruments is described to be an effective action against nosocomial infections. The effectiveness of said method is demonstrated by the use of the kit described in patent application EP2537601 A1, a staining solution which contains Coomassie Blue and a cleaning solution to selectively reveal the biofilms by means of vaporisation.

The accumulation of protein compounds and/or organic materials and/or biofilms not eliminated from medical devices which survive even after sterilisation constitute a real challenge that must be considered in order to reduce the diseases which are formed in hospital environments. It has also been found that the presence of protein compounds on medical devices reduces the effectiveness of sterilisations carried out later. In addition, the presence of these protein compounds increases the adhesion of bacteria such as *Staphylococcus aureus* which could lead to serious diseases and infections.

However, it has been found that current sterilisation techniques are not effective enough to eliminate these protein compounds and/or organic materials and/or biofilms from medical devices.

For this reason, techniques have been recently developed to be able to check the quality of cleaning of medical devices before and/or after their sterilisation. The aim of this is to detect cleaning faults, to be able to correct the problem by identifying medical devices which require additional cleaning and to optimise the cleaning process on an objective basis. Identifying medical devices still contaminated by the presence of protein compounds and/or organic materials and/or biofilms enables these to be eliminated later by carrying out additional cleaning to be able to reuse the devices later, without risk of contamination.

Several techniques exist for identifying protein compounds and/or organic materials and/or biofilms on medical devices such as sampling proteins with a picking solution and quantifying them. This technique consists of sampling medical devices with a contamination disengagement solution and causing the proteins present on the medical devices to react with o-phthaldialdehyde/sodium 2-mercaptoethane-sulphonate to reveal their presence in a laboratory whose aim is to be able to quantify them (see Smith et al. Journal of Foot and Ankle Research 2011, 4:2).

However, these techniques are time consuming and do not allow the areas on the medical devices which need to be treated again to be located. The known methods are expensive, time consuming and do not enable the analysis of a series of medical instruments at once.

An ex situ technique also exists which consists of using a swab which is applied by hand to the surface to be checked. In this way, the proteins are harvested and the degree of contamination is indicated by means of a device dedicated to measuring contamination.

Unfortunately, this technique involves applying the swab to each medical device to be checked, which makes the task tedious for the user who must have one swab per instrument to be analysed. In addition, the area which is potentially contaminated is not necessarily visible or accessible to the operator who may miss the contaminated area. Finally, the recovery rate of the soil present on the instruments by means of this swab is low.

The Synoptics Health company also suggests a machine for detecting proteins called "ProReveal" which consists of analysing medical devices one by one and face by face after spraying a non-toxic fluorescent agent. The user places a single instrument in the machine which, after 3 minutes, checks the quality of cleaning and also enables, by means of fluorescence, the identification of the location of the protein compounds present on the analysed medical device. The analysis can thus be followed by introduction of another medical instrument.

Unfortunately, this method is expensive, slow and impractical, particularly with regards to the number and size of the medical instruments which may be inspected in this way.

In view of the above, there exists a real need to provide a method which can enable the verification of the quality of cleaning applied to the medical devices before and/or after their sterilisation by guaranteeing a quick, practical, reliable, reproducible, effective and inexpensive check.

The present invention more particularly relates to a kit for inspecting the quality of cleaning of a sample, which comprises:

a staining solution by soaking said sample, said staining solution comprising a colorant in a dilution phase, and a developing solution by soaking said sample, said developing solution comprising said dilution phase.

Such a kit has been described in the comparative examples of EP2537601 A1.

Unfortunately, according to this document, it is recommended to use a spray of staining and cleaning solutions earlier because the surfaces to be treated are those of the food industry. In fact, only one face of said surfaces comes into contact with a potential contamination source and must be cleaned. In addition, the kit described in patent application EP2537601 A1 is indicated as being selectively for biofilms, not revealing protein material (see comparative example 1 concerning butter and milk).

However, in a hospital environment, the soils likely to transmit contamination are diverse and are not solely formed of biofilms.

The aim of the invention is to solve this problem by providing a kit which enables the detection of organic soils, whether or not they are formed of biofilms.

A kit for inspecting the quality of cleaning of a sample according to the invention as indicated previously is provided, characterised in that said dilution phase is a dilution phase compatible with the requirements of the medical environment, from which said sample comes, containing one or more medical devices, potentially stained with protein compounds and/or organic materials and/or biofilms present on said medical devices.

Surprisingly, the kit according to the invention enables the checking of the cleaning quality before and/or after sterilisation in a very practical manner, given that a sample contains a series of medical devices which can be analysed simultaneously and very quickly, of the order of a few minutes, with guaranteed reliability and a large detection capacity.

In fact, by using the kit according to the invention, the user wanting to check the quality of cleaning of medical devices first soaks the sample in the first staining solution so the colorant adsorbs onto the protein compounds, and/or the organic materials and/or the biofilms. Then, the stained sample is soaked in the second developing solution to remove the free colorant (excess colorant), in this case the colorant which has not absorbed onto the protein compounds and/or organic materials and/or biofilms present on the medical devices. This step thus reveals the stained zones which should be cleaned again and more deeply in order to completely eliminate these protein compounds and/or organic materials and/or biofilms from these devices.

As such, if nothing is revealed by the appearance of a stain corresponding to the colorant used, the inspection is negative with respect to the detection threshold of the kit according to the invention, i.e. no trace of protein compounds and/or organic materials (soil) and/or biofilms is revealed.

In addition, according to the invention, the dilution phase is compatible with the requirements of the medical environment. Said dilution phase is characterised by a reduced volatility which is very important. In fact, contrary to the food industry which has large halls, the wash rooms of the medical environment are confined and the cleaning team are exposed to vapours throughout the day. It is therefore necessary to reduce the vapours which may be toxic to exposed staff.

This therefore enables the provision of a kit for checking cleaning before and/or after sterilisation which is easy to apply as it does not require additional expensive devices. The use of such a kit is easy to implement on site as, in practice, it is sufficient to have a perforated bucket to immerse in a first container with the staining solution and then in a second container with the developing solution, the first and second containers preferably being equipped with a cover.

The perforated bucket containing the sample is plunged into the staining solution present in the first container for a period of less than 10 minutes, preferably less than 7 minutes, more preferentially ranging from 2 to 5 minutes, even more preferentially equal to 5 minutes.

Said perforated bucket containing the sample is then dried for approximately 30 seconds over the first container. Then said perforated bucket is brought over the second container and is plunged into the developing solution for a period of less than 5 minutes, preferably less than 3 minutes, more preferentially ranging from 0 to 2 minutes, even more preferentially equal to 2 minutes.

Said sample formed of the medical devices is then recovered for identification by means of visible staining.

The sample formed of a series of medical devices is therefore plunged into the first and second containers by means of a perforated bucket which facilitates the transfer from one container to the other.

This demonstrates the ease of implementation and the low cost of using such a kit. In addition, it only requires elements which typically already equip wash rooms.

In a few minutes, the user is able to identify all the soils formed on the analysed medical devices in a very short time, compared to existing devices.

Given that this kit reveals the areas affected on the medical devices by identification by means of visible staining, it is, furthermore, easy to identify invasive and non-invasive areas which are soiled. This aspect also gives a pedagogical advantage to the technology which allows the medical device cleaning teams to be trained and made aware.

The kit according to the invention is also advantageous as it allows the effectiveness of detergent and/or enzymatic compositions to be measured, whose primary aim is to clean or sterilise medical devices. In fact, based on the result obtained by use of the kit according to the invention, it is possible to refine the strength or effectiveness of the cleaning composition based on the medical devices to be treated.

In this way, it is possible to provide different soil cleaning compositions whose effectiveness may be effectively checked, which ultimately allows detergents and/or enzymes to be used wisely, based on the cleaning to be carried out and based on the type of medical devices to be treated. This allows the protocol parameters applied objectively to be adjusted by taking account of (the chemistry of) detergents, contact time, temperature and the mechanical action used.

The kit according to the invention is applied in situ, which constitutes a certain advantage with respect to present techniques given the precise nature of application to the entirety of the surface to be treated is guaranteed at each quality check, which makes the process safe, quick and effective for the user, in the sense that the whole surface of the medical devices is exposed to the colorant of the kit.

The aim of the present invention is to provide a quality control kit which can be used after cleaning of medical devices before and/or after their sterilisation.

In the sense of the present invention, the term "in situ" refers to the act of immersing medical devices in a solution, preferably in an area where they are used or cleaned, and detecting potential sources of contamination directly on the surface of the medical devices. The check specified in the sense of the present invention is carried out by immersing medical devices.

In the sense of the present invention, the term "comprise" may advantageously be replaced by the term "consist of" which enables the exclusion of the presence of any other element defined with respect to the term considered.

In the sense of the present invention, the term "sterilisation" means any method of sterilisation or disinfection of medical devices, such as steam sterilisation, in an autoclave, ethylene oxide sterilisation or any other means whose aim is to completely eliminate microorganisms.

In addition, when a medical device is identified as possessing residual contamination, the fact that the contamination appears coloured facilitates the subsequent cleaning evaluation. In fact, if a medical device displays as positive, it must therefore be cleaned again. As the stain is coloured, the operator can thus directly identify if the second cleaning is sufficient. If any coloured traces remain, the cleaning is insufficient. If no coloured traces remain, and therefore no staining agent, the cleaning is effective. An effective cleaning method is, for example, to place the stained, and therefore coloured, medical devices into an ultrasonic bath containing a detergent composition containing one or more enzymes (proteases, laccases, lipases, amylase, DNase, cellulases, dispersin).

Preferably said staining solution comprises a colorant at a concentration ranging from 0.05% to 1%, preferably at a concentration ranging from 0.05% to 0.5% and more preferentially at a concentration ranging from 0.1% to 0.2%.

More preferentially, said staining solution has a pH ranging between 1 and 9, preferably between 1 and 7, more preferentially between 1 and 5, even more particularly between 1 and 3 or between 3 and 5.

Even more preferably, said dilution phase is an aqueous solution.

Advantageously, said dilution phase comprises at least one acid and water.

More advantageously, said dilution phase further comprises at least one organic solvent. In a particularly advantageous manner, said dilution phase comprises at least one acid chosen from the group consisting of lactic acid, citric acid, acetic acid, oxalic acid, phosphoric acid and potentially at least one organic solvent chosen from the group consisting of ethanol, isopropanol, glycol ethers, ether, acetone, propanol, butanol, petroleum ethers and mixtures thereof.

In a more advantageous manner, said dilution phase comprises at least citric acid and/or lactic acid.

Advantageously, said dilution phase comprises at least one additive and water, said additive, for example, may be an inorganic salt and/or a microbial preservative chosen from the group consisting of ammonium sulphate, sodium chloride, potassium sorbate, methylisothiazoline and sulphite and mixtures thereof.

The list of organic solvents, acids and additives listed above is not exhaustive and may comprise other acids, solvents or additives suitable for forming the dilution phase compatible with the requirements of the medical environment.

According to a preferred embodiment of the kit according to the invention, said medical devices are chosen from the group consisting of dental instruments, surgical instruments with or without lumens, endoscopes and any other medical device, said medical devices being formed of materials of low porosity and/or low roughness. In particular, the materials used in medical devices and in the medical industry are generally stainless steel, titanium, tungsten carbide, chrome-plated materials, plastics, glass, aluminium, anodised aluminium, stainless steel, copper, brass, polyamide-based synthetic materials, polyethylene, PVC, POM, ABS, acrylic glass, polyphenylsulphone, polypropylene, Teflon (PTFE), polycarbonates, in their forms compatible with medical applications and combinations thereof. The medical devices formed of rubber, elastomers, latex, ceramics, wood, naturally strongly coloured surfaces and/or mixtures thereof are excluded due to their porosity and/or roughness.

According to a particular embodiment, the kit according to the invention has a protein detection limit lower than 100 $\mu g/cm^2$, preferably lower than 75 $\mu g/cm^2$.

Other embodiments of the kit according to the invention are specified in the appended claims.

The present invention also relates to a method of quality control for the cleaning of medical devices.

As previously mentioned, methods of checking the quality of the cleaning of medical devices exist.

To solve the problem, it is intended, according to the invention, to provide a method of checking the quality of the cleaning of medical devices comprising the following steps:

providing a sample taken randomly from medical devices, previously cleaned in view of sterilisation, or previously cleaned and sterilised in view of quality control.

bringing said sample into contact with a staining solution which comprises a colorant in a dilution phase compatible with the requirements of the medical environment, checking the quality of cleaning of the sample by means of a potential identification by staining.

Such a method is already known from the Synoptics Health company and has been described previously in this document. Said method is called "ProReveal Protein Detection Test".

Unfortunately, if this method is very effective in terms of quality of detection of proteins, its implementation proves to be significantly more complicated. On the one hand, it requires the expensive installation of a specific machine and therefore additional devices. In addition, the analysis is slow as each face of each medical device must be analysed one by one and this for each medical device separately.

Each medical device is introduced into a machine after having been sprayed by a fluorescent staining solution on one side. Said machine can only analyse one face of one device at a time. Then the medical device must be turned, sprayed again, and put back into the machine in order for the analysis of the medical device to be completed. Furthermore, there is always a risk that, with spraying, the face of the medical device which will be analysed is not completely covered by the fluorescent staining solution.

The analysis carried out by the machine is required to enable identification by fluorescence of protein compounds.

Then, this type of existing method requires the existing washing methods to be adapted, which integrally disrupts the logistic flow in place. The adaptation of the logistic flows in place results in the checking step often being overlooked, as it takes time. The medical environment therefore tends to occasionally be based on its certainties or the tests carried out previously by quality control departments at the time of definition of the logistic flow to be implemented for the cleaning and sterilisation, without carrying out regular checks on the quality of cleaning. However, it is shown that, even after cleaning, parts of medical devices still carry traces of organic soils, which can be sources of contamination to the patient, even after sterilisation, in particular when the organic soils contain biofilm.

A need therefore exists to be able to adapt a method of checking the quality of cleaning in the restricted environment of wash rooms in the medical environment.

The aim of the invention is to solve the problem by procuring a method for checking the quality of cleaning of a sample which is effective, quick and easy to reproduce, and which can be adapted to the wash rooms of medical or hospital environments.

To that end, the method according to the invention is characterised in that said sample comprises one or more randomly chosen medical devices of low porosity and/or low roughness and is placed in a perforated bucket, said contact being carried out by a first soaking by immersing said perforated bucket containing the sample in a staining solution and by a second soaking after staining, by immersing said perforated bucket containing the sample in a developing solution comprising said dilution phase, and in that said identification by staining is a visible stain of protein compounds and/or organic materials and/or biofilms.

Surprisingly, the method according to the invention, as well as being extremely simple to implement in the medical or hospital environment, allows the quality of cleaning to be checked before and/or after sterilisation in a very practical manner. With a very low detection limit and therefore a heighted level of sensitivity, it enables the detection of residual contamination on various medical devices which together form the sample, even in inaccessible areas. This leads to more than considerable time saving which is very important in the medical or hospital environment, and this by using equipment typically present in the medical or hospital environment such as perforated buckets and soak tanks. The tested devices are more numerous and enable a better representation of the contaminated sample.

In the method according to the invention, the medical devices placed in the perforated bucket are plunged into the first soak tank containing the staining solution. Then, said medical devices are plunged, after drying for a few seconds, into the second soak tank containing the developing solution. Said medical devices are then identified by visible staining. These soaking steps enable distribution of the staining solution which is uniform and on all faces of each medical device, including in the tubes.

In addition, according to the invention, the dilution phase is compatible with the requirements of the medical environment. Said dilution phase is characterised by a reduced volatility which is very important. In fact, the wash rooms associated with the medical environment are confined and the cleaning teams are exposed to vapours throughout the day. Consequently, the method according to the present invention enables easy implementation into a very restrictive environment by combining effectiveness and rapidity of detection while ensuring compatibility with the restrictions by using a staining solution whose colorant and dilution phase are effective but lowly toxic or hazardous for users. Said colorant and said dilution phase also facilitate the subsequent cleaning as the traces of soil remain stained until the soil is removed, contrary to the solution used in the "ProReveal" machine which requires the cleanliness to be retested before sterilisation.

Finally, the identification is not limited to the exclusive identification of protein compounds but also includes organic soils and/or biofilms.

Preferably, said first soaking by immersing said perforated bucket containing the sample is carried out for a period of less than 10 minutes, preferably less than 7 minutes, more preferentially ranging from 2 to 5 minutes, even more preferentially equal to 5 minutes.

More preferentially, said second soaking by immersing said perforated bucket containing the sample is carried out for a period of less than 5 minutes, preferably less than 3 minutes, more preferentially ranging from 0 to 2 minutes, even more preferentially equal to 2 minutes.

Advantageously, said first and second soakings by immersing said perforated bucket containing the sample consist of completely immersing said medical devices in the above-mentioned solutions.

According to a preferred embodiment further comprising a step of rinsing, preferably with water, said sample, applied directly after said second soaking, by immersing said perforated bucket containing the sample.

Other embodiments of the method according to the invention are specified in the appended claims.

The present invention also relates to use of the kit according to the present invention to check the quality of cleaning of medical devices before and/or after sterilisation.

Other embodiments of use according to the invention are specified in the appended claims.

The present invention further relates to use of the kit according to the present invention to adjust the cleaning effectiveness of a detergent composition preferably comprising an enzyme.

Other embodiments of this use according to the invention are specified in the appended claims.

Other features, details and advantages of the invention will emerge from the description given above, in a manner which is non-limiting and makes reference to appended examples.

The colorant according to the invention is a colorant chosen from a specific and restricted group such as, for example, Coomassie Blue, Nile red, Amido black 10B, Malachite green and may be of black, red, purple, green, mauve colour, etc. but cannot be methylene blue, fuchsine, crystal violet or Congo red. Indeed, the restricted group has been identified for its specificity to the proteins/polypeptides present in the organic soils and biofilms contaminating the medical devices.

Based on the colorant used, the type of solvent will therefore be chosen to allow, on the one hand, the solubilisation of the colorant and, on the other hand, to be compatible with the requirements of the medical environment and the confined spaces of wash rooms.

It has been found that the dilution phase, such as that of document EP2537601 A1, formed of acetic acid, water and ethanol and isopropanol gives off an odour which is unpleasant and extremely irritating to the staff in the wash rooms.

In the scope of the medical application targeted in the scope of the present invention, it is preferable to provide a dilution phase which does not give off a disagreeable odour.

To do this, it is, for example, possible, based on the colorant, to form the dilution phase according to the invention by mixing water and at least one additive or by mixing citric acid and/or lactic acid or to form the dilution phase by mixing water, ethanol optionally in the presence of isopropanol and citric acid and/or lactic acid to reduce or eliminate this odour which is disagreeable to the user.

It is understood that any other dilution phase may be formed in the scope of the present invention by preparing that dilution phase with other compounds which also enable the provision of a dilution phase which is neutral to the sense of smell.

As can be seen, the dilution phase according to the invention is a phase compatible with the requirements of the medical environment.

In the scope of the present invention, it is also possible to have a single developing and rinsing step by using a water-soluble colorant which would cause the optional additional rinsing step to be removed.

EXAMPLE 1

Skimmed milk is diluted with demineralised water (50 times, 200 times and 300 times). Each drop of each dilution of skimmed milk is deposited on stainless steel swatches. Said swatches are, as a first step, dried for 1 hour at 60° C. and, as a second step, dried for 1 hour at 130° C. The objective of these drying steps is to fix the proteins to their swatches.

Half the swatches are plunged into a staining solution called "staining solution 1" for 5 minutes, the staining solution containing, per 100 ml, 0.1 g Coomassie Blue in a dilution phase comprising approximately 45 g softened water, 40 g ethanol, 10 g isopropanol, 1 g 80% acetic acid, 4 g citric acid.

Half the swatches are then plunged into "developing solution 1", formed of the same dilution phase as staining solution 1, for 2 minutes. The swatches are then air dried.

The other half of the swatches are plunged into a staining solution called "staining solution 2" for 5 minutes, the staining solution containing, per 100 ml, 0.2 g Amido black in a dilution phase comprising approximately 98 g softened water and 2 g citric acid.

Half the swatches are then plunged into "developing solution 2", formed approximately of the same dilution phase as staining solution 2, for 2 minutes. The swatches are then air dried.

The results from example 1 show very satisfactory results concerning the penetration of the Amido black colorant and the sensitivity threshold. Amido black penetrates the swatches with different dilutions tested 50, 200 and 300 times relative to the negative control with a satisfactory intensity. In addition, the results show that the dilution phase does not depend on organic solvents and acetic acid to reach a heighted sensitivity threshold. Furthermore, not using organic solvent or acetic acid enables the vapours from organic solvents and acetic acid which are irritating and toxic to staff to be eliminated.

EXAMPLE 2

Skimmed milk is diluted with demineralised water (50 times, 200 times). Each drop of each dilution of skimmed milk is deposited on stainless steel swatches. Said swatches are, as a first step, dried for 1 hour at 60° C. and, as a second step, dried for 1 hour at 130° C. The objective of these drying steps is to fix the proteins to their swatches.

Half the swatches are plunged into a solution called "solution 1" for 5 minutes, the solution containing, per 100 ml, 0.1 g Coomassie Blue in a dilution phase comprising approximately 70 g softened water, 15 g ethanol, 10 g isopropanol, 5 g lactic acid.

Half the swatches are then plunged into developing solution 1, formed approximately of the same dilution phase as staining solution 1, for 2 minutes. The swatches are then air dried.

The other half of the swatches are plunged into a solution called "solution 2", the solution containing, per 100 g, 0.1 g Coomassie Blue in a dilution phase comprising approximately 70 g softened water, 15 g ethanol, 10 g isopropanol, 1 g acetic acid, 4 g citric acid.

Half the swatches are then plunged into developing solution 1, formed approximately of the same dilution phase as staining solution 1, for 2 minutes. The swatches are then air dried.

The results from example 2 show that the reduction of ethanol from 40 g to 15 g does not reduce the effectiveness. Furthermore, the replacement of the citric acid/acetic acid mixture with lactic acid affects neither the penetration of the colorant nor the detection sensitivity threshold. Coomassie Blue still penetrates the swatches of the different dilutions tested 50 and 200 times with a satisfactory intensity relative to the negative control during the dilution phase containing only 15 g ethanol and when lactic acid was used.

EXAMPLE 3

A staining solution is prepared by mixing 1 g Coomassie Blue in a dilution phase consisting of 450 g water, 400 g ethanol, 100 g isopropanol, 40 g citric acid and 10 g acetic acid. A 5 litre staining solution is prepared by using the above-mentioned measurements multiplied by 5.

A developing solution is prepared with the same elements as those used to form the aforementioned dilution phase, except that a volume of 5 litres is prepared by using the same ratios as those above to form the dilution phase. The developing solution does not contain Coomassie Blue.

5 litres of staining solution are poured into a first tank and 5 litres of developing solution are poured into a second tank.

A perforated bucket containing a sample consisting of 76 dental instruments, among which are 25 tweezers, 46 forceps and 5 microsurgical tweezers.

This perforated bucket containing the sample of dental instruments is completely immersed in the first tank containing the staining solution. The tank is closed with a cover and the bucket is left in this tank for 5 minutes to stain all the dental instruments.

Then, after opening the first tank by removing its cover, the bucket containing the stained sample is completely immersed in the second tank containing the developing solution. This second tank is then closed by another cover and the bucket is left for 2 minutes to remove the excess colorant. This enables the parts of the dental instruments soiled by protein compounds and/or organic materials and/or biofilm to be revealed.

As such, a blue stain visible to the naked eye enables the identification of soiled areas on each instrument checked by the kit according to the invention.

This test has enabled the revelation that 84% of the dental instruments checked contained soil when they came from cleaning and were ready to be sterilised.

This has enabled the application of a subsequent sterilisation/cleaning step in order to completely eliminate the soils identified.

The equipment thus treated has therefore been able to be returned to a line consisting of surgical equipment ready for use.

Preferentially, it is also possible to add a third tank containing water in order to eliminate even more residue.

COMPARATIVE EXAMPLE 1

As in example 3, a staining solution is prepared by mixing 1 g Coomassie Blue in a dilution phase consisting of 450 g water, 400 g ethanol, 100 g isopropanol, 40 g citric acid and 10 g acetic acid. A 1 litre staining solution is prepared by using the above quantities.

A developing solution is prepared with the same elements as those used to form the aforementioned dilution phase. The developing solution does not contain Coomassie Blue. 1 litre of the staining solution is poured into a first spray and 1 litre of the developing solution is poured into a second spray.

30 dental instruments are deposited in a sink, among which are 10 tweezers, 10 forceps and 10 microsurgical tweezers.

The sample of dental instruments is sprayed using the first spray containing the staining solution. The sample of dental instruments is left in open air for 5 minutes until all the dental instruments are stained.

Then the stained sample is sprayed using the second spray containing the developing solution. The sample is left in open air for 2 minutes to remove the excess colorant. This enables the parts of the dental instruments soiled by protein compounds and/or organic materials and/or biofilm to be revealed.

As such, a blue stain visible to the naked eye enables the identification of soiled areas on each instrument checked.

The visual analysis of the instruments shows that the total exposure of the equipment to be evaluated is not ensured. In addition, the parts of the instruments having complex geometries are not correctly exposed to the colorant and the risk of false-negative results has been detected at the hinges of the forceps. In fact, the instruments must be handled and turned for a spray over all the faces of the instruments. The staff are exposed to aerosols via airways and the spray causes contamination of open surfaces.

This test therefore shows that the immersion by soaking instruments in staining and developing solutions enables total exposure of each face of the instruments, an absence of aerosols of staining and developing solutions containing organic solvents and acids in the dilution phase and the immersion by soaking enables a significant amount of time to be gained for cleaning open surfaces as the staining and developing solutions are contained in the soaking tanks.

Spraying as a cleaning quality control technique is therefore dispensed with.

Preferentially, the main embodiment of the present invention is a random check step of the quality of cleaning of medical devices after the cleaning step before sterilisation and/or after the sterilisation step.

Said random inspection step of the quality of cleaning is integrated into the logistic flow of wash rooms. It consists of collecting a sample from a determined number of buckets after cleaning or sterilisation. The determined number of buckets depends on the capacity of the wash room.

A sample is composed of a bucket containing one or more medical devices previously cleaned and/or previously sterilised. Said sample is chosen randomly and tested with the kit for detecting residual contamination.

If a medical device appears to still be soiled, the soil is coloured and this enables viewing, with the naked eye, where there is an area to concentrate on during cleaning to remove the soil.

It is difficult to be able to implement a quality control for all the medical devices for the large structures washing thousands of medical instruments per day. In fact, even if the soaking time is very short, if the quality control is carried out for each medical device, this will cause a significant decrease in the number of cleaned and/or sterilised devices per day.

On the contrary, the invention also provides that, for small structures, such as, for example, in dentistry, the random sampling is systematic. The method of detecting residual contamination by using the kit described in the present invention is therefore implemented after each cleaning.

It is understood that the present invention is in no way limited to the embodiments described above and that modifications may be applied without leaving the scope of the appended claims.

The invention claimed is:

1. A kit for inspecting cleaning quality of a sample, the kit comprising:
   a staining solution by soaking said sample, said staining solution comprising a colorant in a dilution phase, and
   a developing solution by soaking said sample, said developing solution comprising said dilution phase,
   wherein said dilution phase is a dilution phase compatible with requirements of the medical environment, from which said sample comes, containing one or more medical devices, potentially soiled by protein compounds and/or organic materials and/or biofilms present on said medical devices; and
   wherein said staining solution comprises a colorant at a concentration ranging from 0.05% to 1%.

2. The kit according to claim 1, wherein said staining solution has a pH ranging between 1 and 9.

3. The kit according to claim 1, wherein said dilution phase is an aqueous solution.

4. The kit according to claim 1, wherein said dilution phase comprises at least one acid and water.

5. The kit according to claim 1, wherein said dilution phase further comprises an organic solvent.

6. The kit according to claim 1, wherein said dilution phase comprises at least one acid chosen from the group consisting of lactic acid, citric acid, acetic acid, oxalic acid, phosphoric acid and potentially at least one organic solvent chosen from the group consisting of ethanol, isopropanol, glycol ethers, ether, acetone, propanol, butanol, petroleum ethers and mixtures thereof.

7. The kit according to claim 1, wherein said dilution phase comprises at least citric acid and/or lactic acid.

8. The kit according to claim 1, wherein said dilution phase comprises at least one additive and water.

9. The kit according to claim 1, wherein said medical devices are chosen from the group consisting of dental instruments, surgical instruments with or without lumens, endoscopes and any other medical device, said medical devices being of low porosity and/or low roughness are formed of at least one material such as stainless steel, titanium, tungsten carbide, chrome-plated materials, plastics, glass, aluminium, anodised aluminium, stainless steel, copper, brass, polyamide-based synthetic materials, polyethylene, PVC, POM, ABS, acrylic glass, polyphenylsulphone, polypropylene, Teflon (PTFE), polycarbonates, in their forms compatible with medical applications and combinations thereof and which have previously been subjected to cleaning in view of sterilisation.

10. The method according to claim 1, wherein a step of rising with water, said sample is applied directly after said second soaking, by immersing said perforated bucket containing the sample.

11. A method of using the kit according to claim 1, comprising checking quality of cleaning of medical devices.

12. A method of using the kit according to claim 1, comprising adjusting effectiveness of the cleaning of a detergent composition comprising at least one enzyme.

13. A kit for inspecting cleaning quality of a sample, the kit comprising:
   a staining solution by soaking said sample, said staining solution comprising a colorant in a dilution phase; and a developing solution by soaking said sample, said developing solution comprising said dilution phase;

wherein said dilution phase is a dilution phase compatible with requirements of the medical environment, from which said sample comes, containing one or more medical devices, potentially soiled by protein compounds and/or organic materials and/or biofilms present on said medical devices;

the kit having a protein detection limit lower than 100 µg/cm².

14. A method of checking quality of cleaning of medical devices, by using a kit comprising:

a staining solution by soaking said sample, said staining solution comprising a colorant in a dilution phase, and a developing solution by soaking said sample, said developing solution comprising said dilution phase, wherein said dilution phase is a dilution phase compatible with requirements of the medical environment, from which said sample comes, containing one or more medical devices, potentially soiled by protein compounds and/or organic materials and/or biofilms present on said medical devices;

the method comprising the following steps:

providing a sample taken randomly from medical devices, previously cleaned in view of sterilisation, or previously cleaned and sterilised in view of quality control, bringing said sample into contact with a staining solution which comprises a colorant in a dilution phase compatible with the requirements of the medical environment, checking the quality of cleaning of a sample by a potential identification by staining, wherein said sample comprises one or more randomly selected medical devices of low porosity and/or low roughness and is placed in a perforated bucket, said bringing into contact being carried out by a first soaking by immersing said perforated bucket containing the sample into a staining solution, and by a second soaking after staining, by immersing said perforated bucket containing the sample in a developing solution comprising said dilution phase, and wherein said identification by staining is visible staining of protein compounds and/or organic materials and/or biofilms; and wherein said first and second soakings by immersing said perforated bucket containing the sample consist of completely immersing said medical devices in the solutions.

15. The method according to claim 14, wherein said first soaking by immersing said perforated bucket containing the sample is carried out for a period of less than 10 minutes.

16. The method according to claim 14, wherein said second soaking by immersing said perforated bucket containing the sample is carried out for a period of less than 5 minutes.

* * * * *